Figure 1:
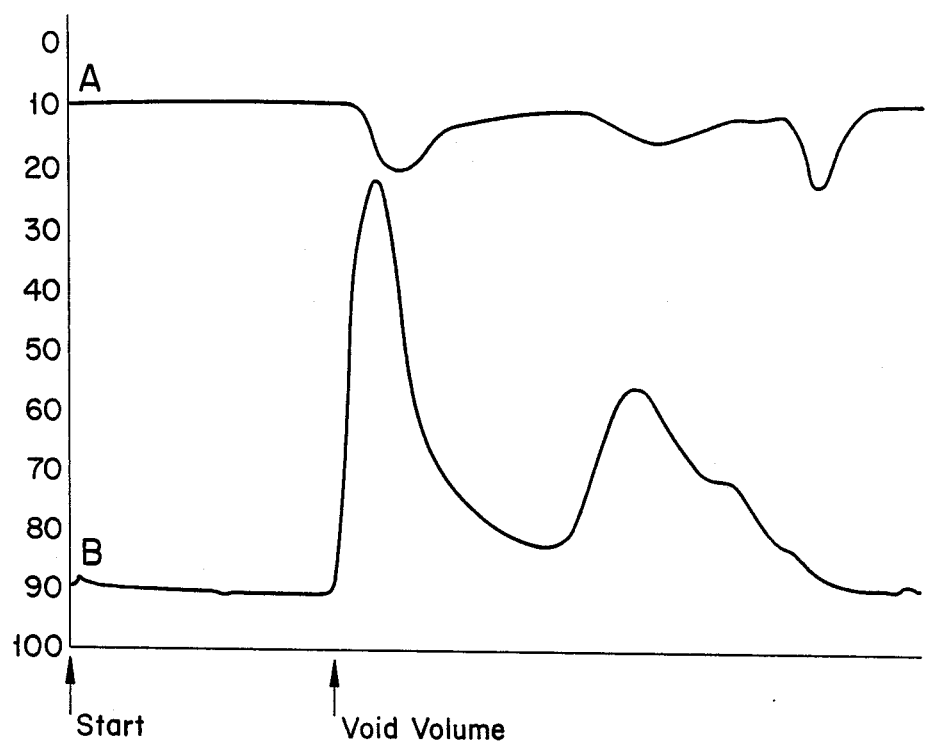

United States Patent [19]

Montie et al.

[11] Patent Number: 4,831,121

[45] Date of Patent: May 16, 1989

[54] POLYDISPERSE NATIVE PSEUDOMONAS FLAGELLAR (H) ANTIGENS (FAG) AND METHODS OF PRODUCING THEM

[75] Inventors: Thomas C. Montie, Knoxville, Tenn.; Friedrich Dorner, Vienna, Austria; James L. McDonel, South Bend, Ind.; Artur Mitterer, Orth/Donau, Austria

[73] Assignee: Immuno Aktiengesellschaft fur chemisch-medizinische Produkte, Vienna, Austria

[21] Appl. No.: 912,242

[22] PCT Filed: Jan. 13, 1986

[86] PCT No.: PCT/AT86/00002

§ 371 Date: Oct. 2, 1986

§ 102(e) Date: Oct. 2, 1986

[87] PCT Pub. No.: WO86/03974

PCT Pub. Date: Jul. 17, 1986

[30] Foreign Application Priority Data

Jan. 14, 1985 [AT] Austria .................................. 72/85

[51] Int. Cl.$^4$ ..................... C07K 15/04; A61K 39/104
[52] U.S. Cl. .................................... 530/350; 530/825; 424/88; 424/92
[58] Field of Search ................... 424/88, 92; 530/350, 530/825, 412, 417, 418, 419, 422, 423, 425

[56] References Cited

U.S. PATENT DOCUMENTS

| | | | |
|---|---|---|---|
| 3,928,565 | 12/1975 | Homma et al. | 424/92 |
| 4,079,126 | 3/1978 | Homma et al. | 424/92 |
| 4,271,147 | 6/1981 | Helting et al. | 530/419 |
| 4,402,939 | 9/1983 | Fournier | 424/92 |
| 4,470,924 | 9/1984 | Iglewski et al. | 424/92 |
| 4,578,458 | 3/1986 | Pier | 424/92 |

FOREIGN PATENT DOCUMENTS 0048422 3/1982 European Pat. Off.

OTHER PUBLICATIONS

Pitt, J. Med. Microbiol, vol. 14, pp. 251–260 (1981). "Flagellar Preparations from *Pseudomonas aeruginosa*: Isolation and Characterization"; Infection and Immunity, Jan. 1982, pp. 281–288, vol. 35, No. 1, Thomas C. Montie, et al.

Chemical Abstracts vol. 103: 139921q: "Electrophoretic Separation and Molecular Weight Characterization of *Pseudomonas aeruginosa* H-Antigen Flagellins", Allison et al.; 1985.

Biological Abstracts vol. 78, No. 71429; "Differentiation of the Major Flagellar Antigens of *Pseudomonas aeruginosa* by the Slide Coagglutination Technique"; Ansorg et al.; 1984.

Microbial Biochem vol. 99: 191185r; "Isolation and Characterization of Flagellar Preparations from *Pseudomonas* species"; Montie et al.; 1983.

(List continued on next page.)

*Primary Examiner*—Delbert R. Phillips
*Assistant Examiner*—Christina Chan
*Attorney, Agent, or Firm*—Burns, Doane, Swecker & Mathis

[57] ABSTRACT

Polydisperse native Pseudomonas flagellar (H) antigens (FAg) and methods of producing them are described, wherein each monomeric component contains certain amino acids, has a certain N-terminal amino acid sequence and a certain molecular weight and is free from pyrogenic substances. The ratio of the individual amino acids in the flagellar antigen of the individual H-serotypes is stated.

For producing the polydisperse native Pseudomonas flagellar (H) antigens (FAg) methods are indicated, wherein *Pseudomonas aeruginosa* bacterial cultures or fractions thereof are treated with a detergent and the flagellar antigens are separated from the cultures. Prior to treatment or in the presence of the detergent, the bacterial culture is subjected to a shearing procedure, i.e. exposed to shearing forces. Thereafter, the flagellar antigens separated from the bacterial mass are isolated by a chromatographic treatment. For this chromatographic treatment a molecular sieve can be used and a further purification by chromatography on a column can be carried out for obtaining flagellar antigens of high purity.

8 Claims, 2 Drawing Sheets

OTHER PUBLICATIONS

Abstracts of the Annual Meeting of the American Society for Microbiology; 1981, vol. 81; B 17, "Protection of Burned, *Pseudomonas* Infected Mice Using Flagellar Preparations"; Montie et al.; 1981.

ZBl.Bakt.Hyg., I. Abt. Orig. A 242,228–238, "Flagella Specific H Antigenic Schema of *Pseudomonas aeruginosa.*"; *1978.*

Medical Microbiology and Immunology 168, 217–226 (1980); "Immunological and Electrophoretic Characterization of Flagellins of Different H-Types of *Pseudomonas aeruginosa*".

1) M-2  a) anti M-2
2) 170018  b) anti 170018
3) 1210  c) anti 1210
4) 5142  d) anti 5142
5) 5940  e) anti 5940
6) 5939  f) anti 5939

1) M-2  a) anti M-2
2) 170018  b) anti 170018
3) 1210  c) anti 1210
4) 5142  d) anti 5142
5) 5940  e) anti 5940
6) 5939  f) anti 5939

POLYDISPERSE NATIVE PSEUDOMONAS FLAGELLAR (H) ANTIGENS (FAG) AND METHODS OF PRODUCING THEM

The invention relates to polydisperse native Pseudomonas flagellar (H) antigens (FAg) and a method of producing them from *Pseudomonas aeruginosa* bacterial cultures.

The bacterium *Pseudomonas aeruginosa* is an opportunistic pathogen which often occurs with hospital infections, mainly in patients having an impaired immune defense, such as patients suffering from burns, persons suffering from cystic fibrosis or having defective organic functions, and in tumor patients. Antibiotics are active against Pseudomonas infections only to a limited extent due to the occurrence of resistances, and therefore attempts have been made to fight infections caused by *Pseudomonas aeruginosa* by immunological methods.

Infections may be triggered by a variety of strains producing O-group antigens and H-antigens. According to the H antigen pattern according to Ansorg (Zbl. Bakt. Hyg. I. Abt. Orig. A 242, 228–238 (1978)), with *Pseudomonas aeruginosa* it is differentiated between a complex flagellar (H) antigen a having the partial antigens $a_0$, $a_1$, $a_2$, $a_3$, $a_4$ and a uniform flagellar (H) antigen b, by using the indirect immunofluorescence technique. The partial factors $a_0$–$a_4$ are independent determinants, so that a flagellar antigen pattern having several H-types results. O-groups and H-type show free combinations.

Strains usable for preparing the *Pseudomonas aeruginosa* bacterial cultures and the antigens produced are listed in the following table.

|   | Strain | H-type |
|---|--------|--------|
| 1 | 170001 | b |
|   | M-2    | b |
| 2 | 5142   | $a_0$ |
| 3 | 5940   | $a_0$, $a_2$ |
| 4 | 5939   | $a_0$, $a_3$ |
| 5 | 5933   | $a_0$, $a_1$, $a_2$ |
|   | 1210   | $a_0$, $a_1$, $a_2$ |
|   | 16990  | $a_0$, $a_1$, $a_2$ |
| 6 | 170018 | $a_0$, $a_3$, $a_4$ |

Isolated filaments of the flagellar antigens, which may be obtained by shaking, homogenization and subsequent centrifugation (R. Ansorg, W. Schmitt, Med. Microbiol. Immunol. (1980) 168: 217–226), are comprised of flagella and flagella fractions, united in a complex comprised of lipopolysaccharides (LPS) and impurities from the nutrient medium; such preparations by their nature are pyrogenic and not suited for an application on man.

It is known to produce Pseudomonas vaccines for preventing Pseudomonas infections, *Pseudomonas aeruginosa* bacterial masses and/or culture filtrates being used as starting materials which were obtained by growing the microorganisms on surface cultures or submersely in complex nutrient media. With these complex nutrient media, various extracts and/or hydrolisates of animal, microbial or vegetable proteins (so-called peptones) were used besides a carbon and energy source (mostly carbohydrates) and essential nutrient salts. Such nutrient solution supplements are not defined as to their precise composition and furthermore are variable from lot to lot. In addition to amino acids, they also contain incompletely decomposed protein fractions and undefined complexes thereof and substantially serve for covering the demand of amino acid and growth-promoting substances. Therefore, culture supernatants are always rich in substances of non-bacterial origin, which has the disadvantage that for preparing a flagellar (H) antigen of *Pseudomonas aeruginosa*, always several separating steps which have to follow the growing step are necessary in order to free the flagellar (H) antigen as far as possible from impurities stemming from the nutrient medium.

The separation of the crude flagellar material from the bacterial suspension was effected by so-called "shearing", i.e. exposure of the bacterial suspension to shearing forces, in a mixer, followed by centrifugation at $15,000 \times g$–$18,000 \times g$. Thereupon, the pellet is discarded and the supernatant containing the crude flagella preparation, is subjected to a centrifugal acceleration of at least $40,000 \times g$ for one hour or $100,000 \times g$ for 20 minutes. Therein the crude antigen is obtained in the form of pellets. As has already been mentioned, it contains i.a. lipopolysaccharides (LPS), nucleic acids, various salts, polysaccharides and non-flagellar proteins which adversely affect the efficiency and compatibility of the vaccines produced therefrom. Hitherto it has not been possible to isolate pure flagellar (H) antigen (T. L. Pitt, J. Med. Microbiol. (1981), 14: 251–260).

The invention aims at avoiding the disadvantages and difficulties described and has as its object to provide polydisperse native flagellar (H) antigens (FAg) of high purity, free from pyrogenic substances.

These highly pure FAg antigens according to the invention are comprised of monomeric components, each component (a) containing the following amino acids: aspartic acid (Asp), threonine (Thr), serine (Ser), glutamic acid (Glu), glycine (Gly), alanine (Ala), valine (Val), isoleucine (Ile), leucine (Leu), thyrosine (Tyr), phenyl alanine (Phe), lysine (Lys), arginine (Arg), and possibly tryptophane (Trp), (b) having the N-terminal amino acid sequence alanine (Ala) - leucine (Leu) - threonine (Thr) - valine (Val) - asparagine (Asn) - threonine (Thr) - asparagine (Asn) - isoleucine (Ile) - alanine (Ala), (c) having a molecular weight of from 43,500 to 53,050 Dalton and (d) being free from proline, methionine, semi-cystine and hystidine.

In detail, according to the invention six specific H-serotypes are characterized, i.e., the flagellar (H) antigen of the H-serotype $a_0$, $a_3$, $a_4$, whose monomeric form contains the amino acids: aspartic acid, threonine, serine, glutamic acid, glycine, alanine, valine, isoleucine, leucine, tyrosine, phenyl alanine, lysine and arginine at a ratio of 64:33:35:42:44:68:29:29:37:3:10:19:15 and has a molecular weight of 43,500;

the flagellar (H) antigen of the H-serotype $a_0$, $a_3$, whose monomeric form contains the amino acids: aspartic acid, threonine, serine, glutamic acid, glycine, alanine, valine, isoleucine, leucine, tyrosine, phenyl alanine, lysine and arginine at a ratio of 69:35:38:44:47:73:30:30:60:3:12:21:16 and has a molecular weight of 46,700;

the flagellar (H) antigen of the H-serotype $a_0$, whose monomeric form contains the amino acids: aspartic acid, threonine, serine, glutamic acid, glycine, alanine, valine, isoleucine, leucine, tyrosine, phenyl alanine, lysine and arginine at a ratio of 74:50:49:49:49::89:37:29:44:5:14:17:16 and has a molecular weight of 52,720;

the flagellar (H) antigen of the H-serotype b, whose monomeric form contains the amino acids: aspartic acid, threonine, serine, glutamic acid, glycine, alanine, valine, isoleucine, leucine, tyrosine, phenyl alanine, lysine and arginine at a ratio of 74:48:48:49:51:91:38:30:43:4:13:18:18 and has a molecular weight of 53,050;

the flagellar (H) antigen of the H-serotype $a_0$, $a_1$, $a_2$, whose monomeric form contains the amino acids: aspartic acid, threonine, serine, glutamic acid, glycine, alanine, valine, isoleucine, leucine, tyrosine, phenyl alanine, lysine and arginine at a ratio of 76:44:40:52:50:81:32:32:41:4:12:20:18 and has a molecular weight of 51,250;

the flagellar (H) antigen of the H-serotype $a_0$, $a_2$, whose monomeric form contains the amino acids: aspartic acid, threonine, serine, glutamic acid, glycine, alanine, valine, isoleucine, leucine, tyrosine, phenyl alanine, lysine and arginine at a ratio of 68:41:37:46:44:73:29:29:37:3:10:16:16 and has a molecular weight of 45,900.

The invention further comprises a method of producing the polydisperse native Pseudomonas flagellar (H) antigens listed from Pseudomonas aeruginosa bacterial cultures, which method comprises treating the bacterial cultures with a detergent and separating the polydisperse native flagellar antigens from the cultures.

By adding the detergent it becomes possible to separate the antigen from the bacterial mass, and the antigens which are in solution then are separated. As detergent, advantageously a salt of the bile acid, in articular deoxycholate, is suitable.

Therein, the bacterial culture can either be disintegrated before it is treated with the detergent, preferably subjected to a "shearing" procedure, or it can be subjected to the shearing forces in the presence of the detergent.

According to a preferred embodiment, the isolation of the polydisperse native flagellar (H) antigens from the bacterial cultures is effected by a chromatographic treatment or purification, the macromolecules present as impurities, in particular the lipopolysaccharides, nucleic acids, salts, polysaccharides and others being retained.

A recommendable modification of the method according to the invention comprises subjecting the disintegrated bacterial culture to a pre-purification prior to the chromatographic treatment, wherein bacteria and microscopically visible bacterial particles are removed from the culture. This pre-purification can be effected by centrifugation with a centrifugal acceleration of up to $5,000 \times g$; the separated sediment is discarded and the supernatant is further processed.

For the chromatographic treatment advantageously a molecular sieve is used which is equilibrated with the detergent. A suitable molecular sieve is Sephacryl.

A further advantageous modification of the method according to the invention comprises subjecting the chromatographically treated and thus purified flagellar antigen to a further purification by chromatography on a column for removing any detergent present, flagellar (H) antigen having a purity of more than 90% being obtained. Also the second chromatographic treatment is carried out with a molecular sieve, such as Sephadex, or with a non-polar polystyrene adsorption gel, such as BIO-BEADS SM-4.

The method according to the invention is explained in more detail by way of the following exemplary embodiment:

A bacterial culture of Pseudomonas aeruginosa M-2 (selected from the bacterial strains listed in the introduction) was developed in a nutrient solution of the following composition:

| | |
|---|---|
| disodium succinate | 4.05 g/l, |
| dipotassium monohydrogen phosphate | 7 g/l, |
| potassium dihydrogen phosphate | 3 g/l, |
| ammonium hydrogen phosphate | 1 g/l, |
| magnesium sulphate.7 $H_2O$ | 0.05 g/l, |
| ferric chloride | 0.0025 g/l, | until a cell density of $2-3 \times 10^9$ cells/ml was reached, and was kept constant at a dilution rate of 0.2 $\mu$ during a fermentation period of 96 hours at an oxygen partial pressure of 10% ($pO_2$) and under stirring.

The bacterial culture continuously withdrawn from the fermentor was worked up in an ultracentrifuge cooperating with the fermentor having a rotor retention capacity of 660 ml (0.45 kg wet mass) at a centrifugal acceleration of $18,000 \times g$, wherein, when using a dilution rate of 0.2 $\mu$, so much biomass had collected after 96 hours that therefrom, after exposure to shearing forces in a mixer, separation of cells and cell fragments at $15,000 \times g-18,000 \times g$ from the pellet of the ultracentrifuge, 149 mg of crude flagellar antigen were obtained.

18 mg of the crude flagellar antigen obtained were dissolved in 12 ml of a 30 mM Tris-HCl buffer solution having a pH of 7.0, to which 20 mg/ml deoxycholate had been added, and applied onto a column of $16 \times 16$ cm that had been filled with Sephacryl S-1000 and which had been equilibrated with the 30 mM Tris-HCl buffer, pH 7.0, to which 2 mg/ml deoxycholate had been added. Thereupon 2 ml fractions were collected and the elution diagram was established by observing the extinctions at 280 and 254 nm. The column run is illustrated in the accompanying diagram (FIG. 1). The curve denoted by A was established at an extinction at 254 nm, and with a cuvette with a light path length of 1 mm; the curve denoted by B was established at an extinction at 280 nm and with a cuvette with a light path length of 20 mm. In the absorption curve the antigen peak is clearly visible at 280 nm.

The solution containing the purified flagellar (H) antigen was then subjected to a second purification step for removing the deoxycholate which had remained from the first purification step, and for this purpose either a molecular sieve having a smaller degree of cross-linking, e.g. Sephadex G-25, is used, or an adsorption gel, such as BIO-BEADS SM-4. With this treatment, the DOC was separated and the flagellar antigen was obtained with a purity of more than 98% and a portion of pyrogenic substances (LPS) of less than 1%.

In the same manner, bacterial cultures of the other strains listed in the introduction can be developed, and the individual H-type antigens can be obtained therefrom in pure form in an analogous manner. It has shown that the yield of FAg is dependent on the selection of the strains. Certain strains, such as 5933 ($a_0$, $a_1$, $a_2$) and 1210 ($a_0$, $a_1$, $a_2$) lead to larger cell yields than 170001 (b) and M-2 (b).

The characteristic data of the individual flagellar (H) antigens characterized according to the invention, which are polymeric compounds and consist of monomeric components, were determined in the following manner:

(A) Amino acid analysis

For analysing the entire amino acid composition of the flagellar (H) antigens, samples were hydrolysed in order to break up the peptide bonds. For this the standard method for protein hydrolysis (6N HCl, 110° C., 22 hours) was used. (C. H. W. Hirs, Methods in Enzymology, S. P. Colowick, N. O. Kaplan, Editors in chief, Volume XI, Enzyme Structure, pp. 59–62, C. H. W. Hirs; ed. 1967, Academic Press).

The tests were carried out in a Beckman system 6300 amino acid analyzer. Based on the resulting amino acid composition, the molecular weight of the monomeric subunits was calculated.

(B) Purity and molecular weight

The purity or freedom from impurities of the antigens according to the invention was checked by polyacrylamide gel electrophoresis in sodium dodecyl sulphate (A. L. Shapiro, E. Vinuela, J. Maizel, Biochem. Biophys. Res. Commun. (1967), 28: 815).

The electropherogram was stained according to the "silverstaining" method (Merril, C. R., Goldman, D., Sedman, S. A. and Ebert, M. H., Science (1981), 211: 1437). With all the examined flagellar antigens only one single band showed which had migrated a certain distance according to the method described below, on the basis of their molecular weights. No hints as to LPS could be found.

Polyacrylamide gel electrophoresis in sodium dodecyl sulphate according to the modification according to Osborn and Weber (Weber, K. and Osborn, M. (1969) J. Biol. Chem. 244: 4406) was used for cleaving the purified flagellar antigens into their monomeric sub-units and for determining their molecular weights.

In the following tables the flagellar (H) antigens of the respective H-serotype, associated to the individual strains, are listed with the corresponding composition of their amino acids and their molecular weights. Tryptophane, if present, is not listed in the table, because it is completely or partially destroyed during the hydrolysis.

| number A.A. | molecule | | | flagellin | | |
|---|---|---|---|---|---|---|
| Strains with associated H-serotype | | | | | | |
| amino acids | 170018 $a_0, a_3, a_4$ | 5939 $a_0, a_3$ | 5142 $a_0$ | M-2 b | 1210 $a_0, a_1, a_2$ | 5940 $a_0, a_2$ |
| aspartic acid | 64 | 69 | 74 | 74 | 76 | 68 |
| threonine | 33 | 35 | 50 | 48 | 44 | 41 |
| serine | 35 | 38 | 49 | 48 | 40 | 37 |
| glutamic acid | 42 | 44 | 49 | 49 | 52 | 46 |
| glycine | 44 | 47 | 49 | 51 | 50 | 44 |
| alanine | 68 | 73 | 89 | 91 | 81 | 73 |
| valine | 29 | 30 | 37 | 38 | 32 | 29 |
| iso-leucine | 29 | 30 | 29 | 30 | 32 | 29 |
| leucine | 37 | 60 | 44 | 43 | 41 | 37 |
| tyrosine | 3 | 3 | 5 | 4 | 4 | 3 |
| phenyl alanine | 10 | 12 | 14 | 13 | 12 | 10 |
| lysine | 19 | 21 | 17 | 18 | 20 | 16 |
| arginine | 15 | 16 | 16 | 18 | 18 | 16 |
| proline | 0 | 0 | 0 | 0 | 0 | 0 |
| methionine | 0 | 0 | 0 | 0 | 0 | 0 |
| semi-cystine | 0 | 0 | 0 | 0 | 0 | 0 |
| histidine | 0 | 0 | 0 | 0 | 0 | 0 |
| Σ = | 450 | 478 | 522 | 525 | 502 | 449 |

| number A.A. | molecule | | | flagellin | | |
|---|---|---|---|---|---|---|
| Strains with associated H-serotype | | | | | | |
| amino acids | 170018 $a_0, a_3, a_4$ | 5939 $a_0, a_3$ | 5142 $a_0$ | M-2 b | 1210 $a_0, a_1, a_2$ | 5940 $a_0, a_2$ |
| MW = | 43,500 | 46,700 | 52,720 | 53,050 | 51,250 | 45,900 |

(C) N-terminal amino acid sequence

With a Beckman-system 890 protein/peptide sequencer, the sequence of the first nine amino acids from the N-terminal end of the purified flagellar (H) antigens was determined with the "solid phase" method (P. Edman, G. Begg, 1967, A protein sequenator, Eur. J. Biochem. 1: 80–91). With all types the same sequence was found.

| | |
|---|---|
| M-2 | Ala-Leu-Thr-Val-Asn-Thr-Asn-Ile-Ala- |
| 5142 | |
| 5939 | |
| 1210 | |
| 170018 | |
| 5940 | |

(D) Particle density of flagellar (H) antigens

The particle density of the flagellar (H) antigens according to the invention was determined by overlaying 1 ml of a sample liquid (flagellar (H) antigen in aqua dest.) to a CsCl-gradient of $d = 1.15-1.45$ g/cm$^3$.

After centrifugation at 50,000 rpm in a Beckman 70 Ti-Rotor for 16 hours, fractions were taken from the bottom of the centrifuge tubes and analysed by means of polyacrylamide gel electrophoresis in sodium dodecyl sulphate.

All the examined flagellar (H) antigen preparations exhibit a density of $d = 1.28$ g/cm$^3$.

(E) Quasi-elastic light scattering

The determination is based on the fact that when laser light acts on a macromolecular solution, the light is scattered by the molecules. The molecules never keep their instantaneous position in the solvent, but move due to Brown's molecular movement. If, for instance, the molecules move away from the laser, the frequency of the scattered light (according to Doppler's effect) will be somewhat lowered. From these shifts of frequency informations about the diffusion of the molecules can be deduced and the "hydrodynamic radius" can be calculated therefrom (Photon correlation spectroscopy and velocimetry, H. Z. Cummins and E. R. Pike, Plenum Press, N.Y., London, 1977).

In the case of the flagellar (H) antigens, the hydrodynamic radius does not represent the radius of the molecule, but a mean size parameter. The latter is, however, very clearly depending on the age of the sample.

The examination conditions applied were: angle of dispersion: 60°, wave length: 632.8 nm, temperature: 20° C. As a result, for all the flagellar antigens: M-2, 5142, 5940, 5939, 1210, 170018, a diffusion coefficient of $D = 8.5 \times 10^{-9}$ (cm$^2$/sec) and a hydrodynamic radius of $R = 2.5 \times 10^{-5}$ cm was obtained.

(F) Immunological analyses

Preparation of immune sera:

Crude, as well as highly purified flagellar antigen preparations were used for immunizing white New Zealand rabbits. The immunization pattern corresponded to the method described by Lagenaur and Agabian (J. Bacteriol. 128: 435–444, 1976). 1 ml, consisting of a 1:1 mixture of flagellar antigen preparation (500

μg/ml) and complete Freund's adjuvans is injected intramuscularly. 20 days after the first injection 4 i.v. injections with 50 μg, 100 μg, 150 μg and 250 μg of the protein preparations in 0.5 ml without adjuvans, were injected at intervals of 3 days. One week after the last immunization blood was taken from the ear vein and allowed to stand at 4° C. The serum was obtained by centrifugation at 4,000×g for 15 minutes and frozen in portions of 0.5 ml at −70° C.

Immunodiffusion:

Immunodiffusion examinations were carried out according to the method of Ouchterlony (O. Ouchterlony, Acta Pathol. Microbiol. Scand. (1949) 26: 507–515) except for the modification described below.

Immunodiffusion was effected on glass plates coated with 1% agarose, containing 1% Triton X-100 in phosphate-buffered saline solution.

The wells for the antibody usually contained 20 μl of serum, the antigen wells contained 1–5 μl of the respective samples. The highly purified flagellar antigen preparations were disintegrated in 0.1% sodium dodecyl sulphate (SDS).

It is difficult for intact flagella to enter into the agarose, and by the treatment with the detergent it was made sure that the antibodies will react with the monomeric antigens. Triton X-100 prevents the precipitation of the antiserum by SDS in the immunodiffusion plates. Immunodiffusion plates are incubated in the humidity chamber at 30° C. for 24 hours.

Immunoelectrophoresis:

The immunoelectrophoresis was effected according to the directions by B. Weeke (A Manual of Quantitative Immunoelectrophoresis, Methods and Application, Axelsen, Kroll, Weeke, eds., Universitetsforlaget, Oslo, 1973, pp. 15–37).

In principle, this method comprises at first electrophoretically separating a protein mixture (in the above case, highly purified flagellar antigen) in a buffered agarose gel by SDS gel electrophoresis, and after the separation procedure, introducing a precipitating immune serum (in the present case, rabbit antiserum to crude and highly purified flagellar (H) antigen) parallel to the migration direction of the separated proteins in one trough.

Antigen and antiserum diffuse subsequently through the agarose gel, which contained 1% Triton X-100, relative to each other, and at their sites of contact arcuate precipitation lines form, whose number, positions and shapes give an insight into the composition of the antigen mixture.

Results of the immunodiffusion:

In the Ouchterlony test the highly purified flagellins each showed one single precipitate band relative to their homologous antiserum, irrespective of whether this antiserum was directed against a crude flagellar antigen preparation or against the highly purified flagellin.

Results of the immunoelectrophoresis:

The immunoelectrophoresis with the highly purified flagellins of the *Pseudomonas aeruginosa* strains M-2, 1210, 5939, 5940, 5142, 170018 exhibited a single precipitate band when using homologous antisera directed against the respective pure flagellar antigen as well as against a crude flagellar antigen preparation.

Figure 2:
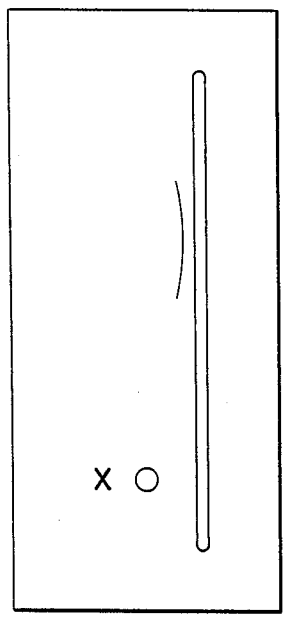
Figure 3:
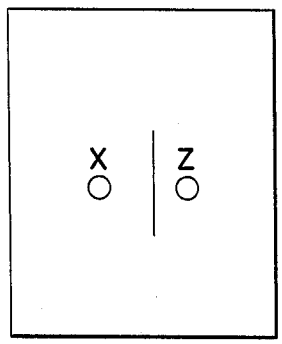

FIG. 2 illustrates the precipitate bands of the one-dimensional immunoelectrophoresis according to Weeke, and FIG. 3 illustrates the precipitate bands of the immunodiffusion according to Ouchterlony.

As can be seen from FIG. 2, the flagellin samples 1 corresponding to strain M-2, 2 corresponding to strain 170018, 3 corresponding to strain 1210, 4 corresponding to strain 5142, 5 corresponding to strain 5940 and 6 corresponding to strain 5939 were each applied to the hole X of the gel strip, and after the electrophoresis, the respective antisera a-f were pipetted in the slot. As illustrated, only one single precipitation band formed, which proves the purity of all six flagellin samples.

According to the illustration in FIG. 3, one test with the pertaining antiserum was carried out for each flagella type M-2, 170018, 1210, 5142, 5940 and 5939. The flagellin sample was each applied in the hole X of the agar plate, and the respective antiserum in the hole Z. Here, too, only one single strong precipitation band occurred, which proves the purity of all six flagellin samples.

We claim:

1. Polydisperse native Pseudomonas flagellar (H) antigen in polymeric form having (i) a diffusion coefficient of $D = 8.5 \times 10^{-9}$ (cm²/sec) (ii) a hydrodynamic radius of $R = 2.5 \times 10^{-5}$ cm, (iii) a density of $d = 1.28$ g/cm³, and (iv) substantial freedom from LPS, said antigen being comprised of monomeric components, each monomeric component
    (a) containing the following amino acids: aspartic acid Asp), threonine (Thr), serine (Ser), glutamic acid Glu), glycine (Gly), alanine (Ala), valine (Val), soleucine (Ile), leucine (Leu) tyrosine (Tyr), phenyl lanine (Phe), lysine (Lys), and arginine (Arg)
    (b) having the N-terminal amino acid sequence alanine (Ala) leucine (Ldu) - threonine (Thr) - valine (Val) - asparagine Asn) - threonine (Thr) - asparagine (Asn) - isoleucine Ile) - alanine (Ala),
    (c) having a molecular weight of from 43,500 to 53,050 and
    (d) being free from proline, methionine, semicystine and histidine.

2. A flagellar (H) antigen of the H-serotype $a_0, a_3, a_4$ according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 64:33:35:42:44:68:29:29:37:3:10:19:15 and has a molecular weight of 43,500.

3. A flagellar (H) antigen of the H-serotype $a_0, a_3$ according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 60:35:38:44:47:73:30:30:60:3:12:21:16 and has a molecular weight of 46,700.

4. A flagellar (H) antigen of the H-serotype $a_0$ according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 74:50:49:49:49:89:37:29:44:5:14:17:16 and has molecular weight of 52,720.

5. A flagellar (H) antigen of the H-serotype b according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 74:48:48:49:51:91:38:30:43:4:13:18:18 and has a molecular weight of 53,050.

6. A flagellar (H) antigen of the H-serotype $a_0$, $a_1,a_2$ according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 76:44:40:52:50:81:32:32:41:4:12:20:18 and has a molecular weight of 51,250.

7. A flagellar (H) antigen of the H-serotype $a_0$, $a_2$ according to claim 1 wherein the monomeric form contains the amino acids: aspartic acid, threonine, serine, glutamic acid, glycine, alanine, valine, isoleucine, leucine, tyrosine, phenyl alanine, lysine and arginine at a ratio of 68:41:37:46:44:73:29:29:37:3:10:16:16 and has a molecular weight of 45,900.

8. The flagellar (H) antigen according to claim 1 wherein each monomeric component contains tryptophane (Trp).

* * * * *

UNITED STATES PATENT AND TRADEMARK OFFICE
CERTIFICATE OF CORRECTION

PATENT NO. : 4,831,121

DATED : May 16, 1989

INVENTOR(S) : Thomas C. Montie et al.

It is certified that error appears in the above-identified patent and that said Letters Patent is hereby corrected as shown below:

Column 3, line 2, "49::89" should read -- 49:89 --;

line 34, "in articular" should read -- in particular --;

Column 5, line 14, "6300amino" should read -- 6300 amino --;

In the table, under the column amino acid, "iso-" should read

-- isoleucine --;

Column 8, line 27, "Asp)" should read -- (Asp) --;

line 28, "Glu)" should read -- (Glu) --;

line 29, "soleucine" should read -- isoleucine --;

line 30, "phenyl lanine" should read -- phenyl alanine --;

line 33, "(Ala) leucine" should read -- (Ala) - leucine -- and

"(Ldu)" should read -- (Leu) --;

line 34, "Asn)" should read -- (Asn) --;

line 35, "Ile)" should read -- (Ile) --; and line 52, "60:35..." should read -- 69:35... --.

Signed and Sealed this

Twenty-ninth Day of May, 1990

Attest:

HARRY F. MANBECK, JR.

*Attesting Officer*          *Commissioner of Patents and Trademarks*